(12) United States Patent
Rebec et al.

(10) Patent No.: US 9,554,735 B2
(45) Date of Patent: Jan. 31, 2017

(54) METHOD FOR BUILDING AN ALGORITHM FOR CONVERTING SPECTRAL INFORMATION

(71) Applicant: Ascensia Diabetes Care Holdings AG, Basel OT (CH)

(72) Inventors: Mihailo V. Rebec, Bristol, IN (US); James E. Smous, Niles, MI (US); Steven D. Brown, Newark, DE (US); Hu-Wei Tan, Cambridge, MA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 13/871,116

(22) Filed: Apr. 26, 2013

(65) Prior Publication Data
US 2013/0261406 A1 Oct. 3, 2013

Related U.S. Application Data

(62) Division of application No. 11/973,790, filed on Oct. 10, 2007, now Pat. No. 8,452,359, which is a division
(Continued)

(51) Int. Cl.
*A61B 5/1455* (2006.01)
*A61B 5/145* (2006.01)
(Continued)

(52) U.S. Cl.
CPC ......... *A61B 5/14532* (2013.01); *A61B 5/1455* (2013.01); *A61B 5/1495* (2013.01);
(Continued)

(58) Field of Classification Search
CPC . A61B 5/1455; A61B 5/14532; A61B 5/0059; A61B 5/14552
(Continued)

(56) References Cited

U.S. PATENT DOCUMENTS 4,526,568 A * 7/1985 Clemens et al. ............ 604/4.01
4,975,581 A 12/1990 Robinson et al.
(Continued)

FOREIGN PATENT DOCUMENTS

EP 0 404 562 8/1998
EP 1 335 199 A1 8/2003
(Continued)

OTHER PUBLICATIONS

Haaland et al., "Reagentless Near-Infrared Determination of Glucose in Whole Blood Using Multivariate Calibration," *Applied Spectroscopy*, vol. 46, No. 10, 1992, pp. 1575-1578.
(Continued)

*Primary Examiner* — Tse Chen
*Assistant Examiner* — Chu Chuan (JJ) Liu
(74) *Attorney, Agent, or Firm* — Nixon Peabody LLP

(57) ABSTRACT

A system for determining the concentration of an analyte in at least one body fluid in body tissue comprises an infrared light source, a body tissue interface, a detector, and a central processing unit. The body tissue interface is adapted to contact body tissue and to deliver light from the infrared light source to the contacted body tissue. The detector is adapted to receive spectral information corresponding to infrared light transmitted through the portion of body tissue being analyzed and to convert the received spectral information into an electrical signal indicative of the received spectral information. The central processing unit is adapted to compare the electrical signal to an algorithm built upon correlation with the analyte in body fluid, the algorithm adapted to convert the received spectral information into the concentration of the analyte in at least one body fluid.

5 Claims, 8 Drawing Sheets

Related U.S. Application Data of application No. 10/361,895, filed on Feb. 11, 2003, now Pat. No. 7,299,079.

(60) Provisional application No. 60/355,358, filed on Feb. 11, 2002.

(51) Int. Cl.
*A61B 5/1495* (2006.01)
*G01N 21/359* (2014.01)
*A61B 5/00* (2006.01)
*G01N 21/27* (2006.01)

(52) U.S. Cl.
CPC ............ *G01N 21/359* (2013.01); *A61B 5/726* (2013.01); *G01N 21/274* (2013.01); *G01N 2201/067* (2013.01)

(58) Field of Classification Search
USPC .... 600/310, 316, 322, 331, 365, 473; 436/8, 436/14, 164; 356/39
See application file for complete search history.

(56) References Cited

U.S. PATENT DOCUMENTS

| | | | |
|---|---|---|---|
| 5,039,855 A | 8/1991 | Kemeny et al. | |
| 5,090,418 A | 2/1992 | Squires et al. | |
| 5,099,123 A | 3/1992 | Harjunmaa | |
| 5,120,961 A | 6/1992 | Levin et al. | |
| 5,137,023 A | 8/1992 | Mendelson et al. | 600/316 |
| 5,178,142 A | 1/1993 | Harjunmaa et al. | 600/310 |
| 5,179,951 A | 1/1993 | Knudson | |
| 5,183,042 A | 2/1993 | Harjunmaa et al. | |
| 5,348,003 A | 9/1994 | Caro | |
| 5,370,114 A | 12/1994 | Wong et al. | |
| 5,372,135 A | 12/1994 | Mendelson et al. | |
| 5,435,309 A | 7/1995 | Thomas et al. | |
| 5,477,321 A | 12/1995 | Johnson | |
| 5,560,356 A | 10/1996 | Peyman | |
| 5,571,401 A | 11/1996 | Lewis et al. | |
| 5,606,164 A | 2/1997 | Price et al. | |
| 5,636,633 A | 6/1997 | Messerschmidt et al. | |
| 5,655,530 A | 8/1997 | Messerschmidt | |
| 5,710,630 A | 1/1998 | Essenpreis et al. | |
| 5,750,994 A | 5/1998 | Schlager | |
| 5,815,277 A | 9/1998 | Zare et al. | |
| 5,823,951 A | 10/1998 | Messerschmidt | |
| 5,830,132 A | 11/1998 | Robinson | |
| 5,935,062 A | 8/1999 | Messerschmidt et al. | |
| 5,957,841 A * | 9/1999 | Maruo et al. | 600/316 |
| 5,978,691 A | 11/1999 | Mills | |
| 6,061,582 A * | 5/2000 | Small et al. | 600/316 |
| 6,064,897 A | 5/2000 | Lindberg et al. | |
| 6,070,093 A | 5/2000 | Oosta et al. | |
| 6,101,405 A | 8/2000 | Yasuda et al. | |
| 6,119,026 A | 9/2000 | McNulty et al. | |
| 6,157,041 A * | 12/2000 | Thomas et al. | 250/573 |
| 6,172,743 B1 | 1/2001 | Kley et al. | |
| 6,219,565 B1 | 4/2001 | Cupp et al. | |
| 6,222,189 B1 | 4/2001 | Misner et al. | |
| 6,241,663 B1 | 6/2001 | Wu et al. | |
| 6,278,889 B1 | 8/2001 | Robinson | |
| 6,309,884 B1 * | 10/2001 | Cooper et al. | 436/14 |
| 6,370,406 B1 | 4/2002 | Wach et al. | |
| 6,441,388 B1 * | 8/2002 | Thomas et al. | 250/573 |
| 6,725,073 B1 | 4/2004 | Motamedi et al. | |
| 7,308,293 B2 | 12/2007 | Gerlitz | |
| 2002/0016534 A1 | 2/2002 | Trepagnier et al. | |
| 2004/0092804 A1 | 5/2004 | Rebec et al. | |

FOREIGN PATENT DOCUMENTS

| | | | |
|---|---|---|---|
| GB | 2 328 279 | 2/1999 | |
| JP | 2000/186998 | 7/2000 | ............ G01N 21/17 |
| WO | WO 99/59464 | 11/1999 | ............ A61B 5/00 |
| WO | WO 00/74753 | 12/2000 | |
| WO | WO 01/67946 A1 | 9/2001 | ............ A61B 5/00 |
| WO | WO 02/84237 A1 | 10/2002 | |
| WO | WO 2005/004712 A1 | 1/2005 | |

OTHER PUBLICATIONS

Robinson et al., "Noninvasive Glucose Monitoring in Diabetic Patients: A Preliminary Evaluation," *Clinical Chemistry*, vol. 38, No. 9, 1992, pp. 1618-1622.

Marbach et al., "Noninvasive Blood Glucose Assay by Near-Infrared Diffuse Reflectance Spectroscopy of the Human Inner Lip," *Applied Spectroscopy*, vol. 47, No. 7, 1993, pp. 875-881.

Danzer et al., "Non-invasive Determination of Glucose by NIR Reflectance Measurements and Chemometric Evaluation," Source unknown, date unknown, 4 pgs.

Tran et al., "Electronic Tuning, Amplitude Modulation of Lasers by a Computer-Controlled Acousto-optic Tunable Filter," *Applied Spectroscopy*, vol. 46, No. 7, 1992, pp. 1092-1095.

Burmeister et al., "Evaluation of Measurement Sites for Noninvasive Blood Glucose Sensing with Near-Infrared Transmission Spectroscopy," *Clinical Chemistry*, vol. 45, 1999, pp. 1621-1627.

Mackenzie et al., "Advances in Photoacoustic Noninvasive Glucose Testing," *Clinical Chemistry*, vol. 45, 1999, pp. 1587-1595.

Malin et al., "Noninvasive Prediction of Glucose by Near-Infrared Diffuse Reflectance Spectroscopy," *Clinical Chemistry*, vol. 45, 1999, pp. 1651-1658.

Khalil, "Spectroscopic and Clinical Aspects of Noninvasive Glucose Measurements," *Clinical Chemistry*, vol. 45, No. 2, 1999, pp. 165-177.

Cameron et al., "The Use of Polarized Laser Light Through the Eye for Noninvasive Glucose Monitoring," *Diabetes Technology & Therapeutics*, vol. 1, No. 2, 1999, pp. 135-143.

Editorial; "Noninvasive Laser Measurement of Blood Glucose in the Eye: A Bright Idea or an Optical Illusion?," *Diabetes Technology & Therapeutics*, vol. 1, No. 2, 1999, pp. 117-119.

Ward et al., "Post-Prandial Blood Glucose Determination by Quantitative Mid-Infrared Spectroscopy," *Applied Spectroscopy*, vol. 46, No. 6, 1992, pp. 959-965.

Pan et al., "Near-Infrared Spectroscopic Measurement of Physiological Glucose Levels in Variable Matrices of Protein and Triglycerides," *Analytical Chemistry*, vol. 68, No. 7, Apr. 1, 1996, pp. 1124-1134.

Sowa et al., "Noninvasive Assessment of Regional and Temporal Variations in Tissue Oxygenation by Near-Infrared Spectroscopy and Imaging," *Applied Spectroscopy*, vol. 51, No. 2, 1997, pp. 143-152.

Müller et al., "Non-invasive blood glucose monitoring by means of near infrared spectroscopy: methods for improving the reliability of the calibration models," *The International Journal of Artificial Organs*, vol. 20, No. 5, 1997, pp. 285-290.

Borchert, et al., "A Noninvasive Glucose Monitor: Preliminary Results in Rabbits," *Diabetes Technology & Therapeutics*, vol. 1, No. 2, 1999, pp. 145-151.

Youcef-Toume et al., "Noninvasive Blood Glucose Analysis Using Near Infrared Absorption Spectroscopy," *MIT Home Automation and Healthcare Consortium*, Progress Report No. 2-5: Mar. 31, 2000, pp. 1-7.

T. Fearn, "On Orthogonal Signal Correction," *Chemometrics and Intelligent Laboratory Systems*, 50 (2000), pp. 47-52.

Small, "Strategies for Coupling Digital Filtering With Partial Least-Squares Regression: Application to the Determination of Glucose in Plasma by Fourier Transform Near-Infrared Spectroscopy," *Anal. Chem.* 1993, 65, pp. 3279-3289.

* cited by examiner

METHOD FOR BUILDING AN ALGORITHM FOR CONVERTING SPECTRAL INFORMATION

CROSS-REFERENCE TO RELATED APPLICATIONS

This application is a divisional of U.S. patent application Ser. No. 11/973,790 filed Oct. 10, 2007; U.S. patent application Ser. No. 11/973,790 is a divisional of U.S. patent application Ser. No. 10/361,895 filed Feb. 11, 2003, issued on Nov. 20, 2007 as U.S. Pat. No. 7,299,079 B2, which claims priority to Provisional Application No. 60/355,358 filed on Feb. 11, 2002, all of which are incorporated by reference in their entireties.

FIELD OF THE INVENTION

The present invention relates generally to systems for the determination of analytes in body fluids, and, more particularly, to a system for the non-invasive determination of analytes in body fluids.

BACKGROUND OF THE INVENTION

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

Common methods for monitoring a person's blood glucose level are invasive in nature. Typically, in order to check the blood glucose level, a drop of blood is obtained from the fingertip using a lancing device. The blood drop is produced on the fingertip and the blood is harvested using the test sensor. The test sensor, which is inserted into a testing unit, is brought into contact with the blood drop. The test sensor draws the blood to the inside of the test unit which then determines the concentration of glucose in the blood.

One problem associated with this type of analysis is that there is a certain amount of pain associated with the lancing of a finger tip. Diabetics must regularly self-test themselves several times per day. Each test requires a separate lancing, each of which involves an instance of pain for the user. Further, each lancing creates a laceration in the users skin which take time to heal and are susceptible to infection just like any other wound.

Other techniques for analyzing a person's blood glucose level are noninvasive in nature. Commonly, such techniques interpret the spectral information associated with light that has been transmitted through or reflected from a person's skin. An advantage of this type of noninvasive analysis is that there is no associated pain or laceration of the skin. However, thus far, such techniques have proven unreliable because many techniques fail to recognize the many issues which impact the analysis. For example, many noninvasive reflectance and transmission based systems do not account for the fact the obtained spectral data contain glucose information from the portion of body tissue being analyzed as a whole, and is not limited to blood glucose. Other techniques do not account for irregularities in the spectral signal of the analyte due to instrumental drift, temperature changes in the tissue under analysis, spectral characteristics of the tissue that change due to pressure changes, etc. that can occur during the analysis or between analysis. These irregularities can impact the quality of the calibration model or the algorithms that used to determine the analyte concentrations from the non-invasively collected spectral data. The spectral data that has these irregularities can not be used by the algorithms to determine the analyte concentrations.

Accordingly, there exists a need for a reliable noninvasive system for the determination of analytes in body fluids.

SUMMARY OF THE INVENTION

A system for determining the concentration of an analyte in at least one body fluid in body tissue comprises an infrared light source, a body tissue interface, a detector, and a central processing unit. The body tissue interface is adapted to contact body tissue and to deliver light from the infrared light source to the contacted body tissue. The detector is adapted to receive spectral information corresponding to infrared light transmitted through the portion of body tissue being analyzed and to convert the received spectral information into an electrical signal indicative of the received spectral information. The central processing unit is adapted to compare the electrical signal to an algorithm built upon correlation with the analyte in body fluid, the algorithm adapted to convert the received spectral information into the concentration of the analyte in at least one body fluid.

The above summary of the present invention is not intended to represent each embodiment, or every aspect, of the present invention. Additional features and benefits of the present invention will become apparent from the detailed description, figures, and claim set forth below.

BRIEF DESCRIPTION OF THE FIGURES

Other objects and advantages of the invention will become apparent upon reading the following detailed description in conjunction with the drawings in which:

FIG. 5b is a cross-sectional view taken along line 5b of FIG. 5a;

FIG. 6 is a plot of the absorbency of reflection light versus wavelength of the reflected light according to one embodiment of the reflected-based system illustrated in FIG. 5a; and FIG. 7 is a plot of predicted glucose concentration versus the measured glucose concentration according to one embodiment of the reflection-based system illustrated in FIG. 5a.

DETAILED DESCRIPTION OF THE ILLUSTRATED EMBODIMENTS

Figure 1:
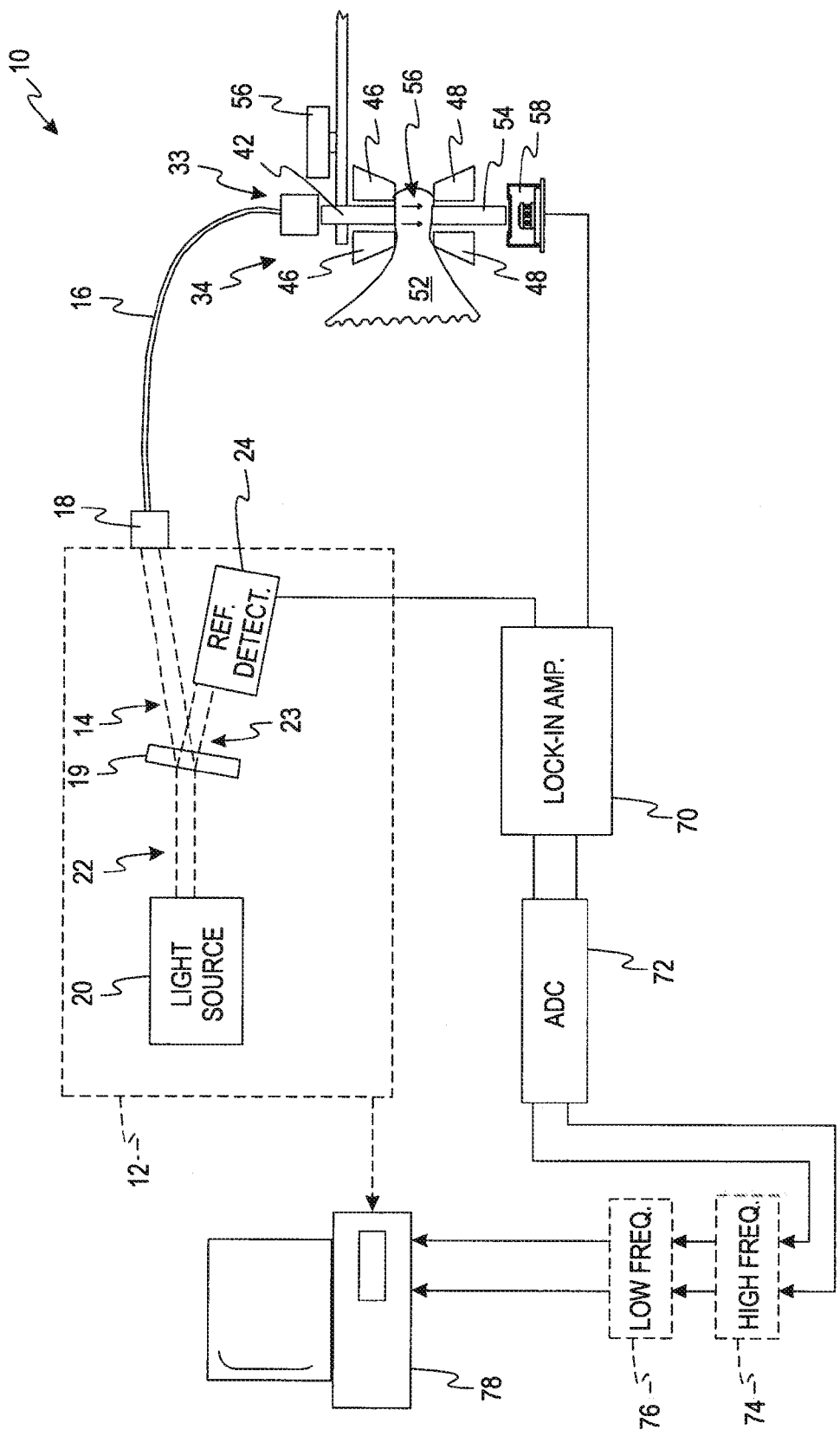
FIG. 1 is a functional block diagram of a transmission-based system for determining analytes in body fluids according to one embodiment of the present invention.

Referring to the drawings and initially to FIG. 1, a transmission-based non-invasive system 10 ("the system 10") for the determination of analytes in body fluids is functionally illustrated. While the present invention will be discussed in connection with determining a patient's glucose level, the present invention is applicable in the analysis of any analyte in body fluid that exhibits spectral characteristics. Briefly, the system 10 inputs near infrared light to a piece of skin, such as the "web" of skin between a patient's index finger and thumb, and records the light transmitted through that piece of skin in order to determine the patient's glucose level. Conventionally, a patient's glucose level is referred to as a patient's blood-glucose level. However, to refer to a blood glucose level implies ignoring the amount of glucose contained in a patient's extra-cellular material and inter-cellular material. Accordingly, the inventors of the present invention prefer to refer to a patient's glucose level.

Human skin is made of approximately fifty to sixty percent intercellular material with the balance comprising extracellular material. The extracellular material comprises approximately one-third plasma (blood) and about two-thirds interstitial fluid ("ISF"). Therefore, when examining the spectral characteristics of glucose from light that is transmitted though a patient's skin, it is important to consider glucose in that portion of skin as a whole, rather than solely the glucose in a patient's blood. The largest portion of the transmitted light is made up of light transmitted though ISF, and not blood. Conversely, in an invasive setting where a 10 μl drop of blood is obtained on a patient's finger tip, for example, the determined glucose concentration primarily represents the concentration of glucose in that patient's blood.

The system 10 is used to obtain transmitted spectral information from a patient. For example, the system 10 is used in a test wherein the glucose concentration of the test subject is modulated to a plurality of different concentration levels. One such test is a glucose clamping test where the glucose level of the test subject is raised and lowered to various levels over the duration of the test. According to one embodiment, the glucose clamping test is designed to bring the test subject's glucose level to six plateau regions that range in concentration from 50 to 300 mg/dl. Each plateau is separated by about 50 mg/dl so that each region can be clearly differentiated. ISF and plasma samples are collected throughout the duration of the clamping test. The samples are collected every five minutes and are analyzed for glucose content. This measurement is used to adjust the infusion of glucose or insulin to maintain the glucose concentration of the plasma for about twenty-five minutes at a particular targeted plateau region. Very generally, the spectral data obtained over the course of the test are compared to the actual glucose levels (determined using invasive techniques) obtained during the test. From this data, a calibration algorithm is built to predict the actual glucose level of the patient based on the spectral characteristics of light transmitted through that patient's skin. This calibration algorithm can then be incorporated into a handheld version of the system 10 illustrated in FIG. 1.

Such a handheld instrument would enable a user to noninvasively monitor the user's glucose concentration level. The user would contact the user's skin with the instrument to obtain spectral information from the user's skin. The instrument would then provide the user with a reading of the user's glucose concentration level a short time later.

Referring back to FIG. 1, an acoustic-optic tunable filter ("AOTF") spectrometer is shown generally by dashed line 12. The AOTF spectrometer 12 outputs a monochromatic, modulated beam of light 14 into a fiber optic cable 16 via a lens 18. The AOTF spectrometer 12 includes a light source 20. According to one embodiment, the light source 20 is a Tungston-Halogen light source, which is a low-cost, stable light source that outputs a good amount of light (e.g., 275 watts). Alternative light sources include light emitting diodes ("LED"), doped fibers including uranium doped fibers, and laser diodes. The light source produces a beam of light 22 in the near-infrared region (i.e., having a wavelength ranging 750-2500 nanometers).

Generally, the AOTF spectrometer 12 functions as an electronically tunable spectral band-pass filter to output the monochromatic beam of light 14 having wavelengths within a desired range. The AOTF 12 is a solid state electro-optical device that consists of a crystal 19 in which acoustic (vibrational) waves, at radio frequencies ("RF") are used to separate a single wavelength of light from a broadband light source. The wavelength selection is a function of the frequency of the RF applied to the crystal 19. The crystal 19 used in AOTF devices can be made from a number of compounds. According to one embodiment of the present invention, the crystal of Tellurium Dioxide (TeO$_2$). TeO$_2$ crystals providing good results for use with light in the 1200 to 3000 nm spectral region. According to one embodiment, the crystal 19 is used in a non-collinear configuration, wherein the acoustic and optical waves (paths) through the crystal 19 are at very different angles from each other. A transducer (not shown) is bonded to one side of the crystal. This transducer emits vibrations (acoustic waves) when RF is applied to the transducer. As the acoustic waves from the transducer to the crystal 19, the crystal 19 alternately compresses and relaxes resulting in a refractive index variation that acts like a transmission diffraction grating. Unlike a classical grating, however, the crystal only diffracts one specific wavelength of light so it acts like a filter more than a diffraction grating. The wavelength of the light that is diffracted is determined by a phase matching condition based on the birefringence of the TeO$_2$ crystal and the velocity and frequency of the acoustical wave and as well as parameters specific to the design of the AOTF. The wavelength that is selected is varied by simply changing the frequency of the applied RF. The diffracted light is directed into two first order beams that we called the positive and negative beams. The rest of the undiffracted light is passed through as undiffracted zero (0) order beam. The two positive and negative beams are orthogonally polarized. The positive beam is delivered to the optoid as described below and the negative beam is used as a reference beam to correct for variations in the intensity of the light source or the efficiency of the AOTF as described below.

According to one embodiment, the beam of light 14 output by the AOTF spectrometer has a resolution or bandwidth of about four to ten nanometers ("nm"). This bandwidth is swept (back and forth) across a wavelength range of about 1400 to 2500 nanometers. Put another way, the AOTF spectrometer 12 outputs light having a wavelength continuously ranging between 1400 and 2500 nm and has a resolution of 4-10 nm. The timing of the sweep can range from about one second to several seconds. A suitable AOTF spectrometer is available from Crystal Technologies, Inc. of Palo Alto, Calif. as AOTF Model 2536-01. The AOTF spectrometer includes a RF driver, a mixer, and a low frequency oscillator (not shown) for modulating the monochromatic beam of light 14 at approximately 20,000 Hz. A voltage control oscillator (not shown) provides the control of the RF frequency. Separate circuitry (not shown) is used for modulation and power control, which range from 0 to about 0.5 watts. A suitable voltage control oscillator is available from the Inrad Corporation, Northvale, N.J., Model DVCO-075A010. The power is delivered to an acoustical transducer that creates an acoustical wave that changes the characteristic of a birefringence crystal 19 so that full spectrum light is separated to wavelengths associated with a particular frequency and the rest of the light passes through as zero order light.

The crystal 19 of the AOTF spectrometer 12 splits the beam of light 22 into the first beam 14 and a second beam 23. The second beam of light 23 is directed to a reference detector 24 for measuring/recording the light input to the skin. Additionally, the reference detector 24 measures/records the light 23 for instrument drift associated with the light source and AOTF that can occur over time due to the length of operating time and change in temperature of the instrument over that time period.

The light 14 output by the AOTF spectrometer 12 is directed into a lens 18 that reduces the diameter of the beam of light and focuses the beam of light 14 into an end of the fiber optic cable 16. The lens 18 effectively couples the AOTF spectrometer 12 to the fiber optic cable 16. The fiber optic cable 16 is a low OH (i.e., preferably about 0.3 parts per million of in silica) fiber optic cable which has high attenuation over the length of the cable. The more OH the greater the intrinsic absorbance of the fiber itself especially in the wavelength region above 2100 nm. According to another embodiment, the fiber optic cable has a OH of less than about 0.12 ppm. The quality of light input to the fiber optic cable 16 is substantially maintained when delivered to a patient's skin at an opposite end 33 of the fiber optic cable 16. The output end 33 of the fiber optic cable 16 connects to a device the inventor has termed an optoid 34. Generally, the optoid 34 consists of the hardware that interfaces with the patient's skin. The optoid 34 includes a first plate 46 and a second plate 48, which are slideably clamped onto the tissue being analyzed, such as the web of skin 52 ("the web 52") of a patient's hand between the index finger and thumb. The optoid 34 includes a sapphire rod 42 that delivers light from the fiber optic cable 16 to the web 52. The sapphire rod 42, having a diameter of about three millimeters in one embodiment, increases the diameter of the beam of light input to the web 52. Fiber optic cables are typically limited in diameter to about two millimeters. The larger diameter of the sapphire rod 42 provides an effective means of coupling light that can be up to 3 mm in beam diameter to be delivered to the skin. Delivering a wider beam of light (e.g., the 3 mm of the sapphire rod as opposed to the 2 mm diameter of the fiber optic cable) covers a larger area of skin which limits the impact of small irregularities in skin properties. The sapphire rod 42 is flush with the interior surface of the first plate 46.

The light that is directed into the web 52 via the sapphire rod 42 is transmitted through the web 52 and into a second sapphire rod 54 (also 3 mm in diameter) disposed within the second plate 48. The light passing through the web 52 is generally represented by arrows 56. The amount of light transmitted through the web 52 is very low. Typically, less than about two percent of the light exiting the first sapphire rod 42 enters into the second sapphire rod 54. The light transmitted through the web 52 is directed by the second sapphire rod 54 into a detector 58. According to one embodiment of the present invention, the detector 58 is an extended Indium Gallium Arsenate ("InGaAs") detector having a circular active surface of three millimeters in diameter and provides a response across the 1300 to 2500 nm spectral region. Such a detector is commercially available from the Hamamatsu Corporation. According to one embodiment of the present invention, the reference detector 24 and the detector 58 are the same type of detector. Examples of other types of detectors that can be used in alternative embodiments of the present invention include Indium Arsenide ("InAs"), Indium Selenide ("InSe"), Lead Sulfide ("PbS"), Mercury-Cadmium-Telluride ("MCT"), and DTG detectors. Other types of detectors can be used depending on the desired region of the spectrum to be analyzed for determining the glucose concentration level. As is discussed in greater detail below in connection with FIG. 2, glucose exhibits unique spectral characteristics in the about 1450-1850 nm and the about 2200-2500 nm spectral range. The detector 58 generates an electrical signal indicative of the detected transmitted light, which is processed as is described in detail below. In addition to providing a mechanism for transmitting light through the web 52, the optoid 34 performs other mechanical functions. First, the moveable first and second plates 46 (also referred to as "jaws") provide pressure to compress the web 52 in order to maintain a consistent optical path through the web 52. Compressing the web 52 brings a greater consistency to the testing process. According to one embodiment, the plates 46,48 compress the tissue approximately six percent. Compressing the tissue also creates a flush interface between the web of skin and the plates 46,48 by eliminating air gaps between the web and plates 46,48 so that the light transmitted from the first sapphire rod 42 directly enters the web 52. The optoid 34 includes a load cell 56 to measure the contact pressure on the web of skin 52. During the analysis, pressure measurements and temperature measurements are obtained so that irregularities associated with changes in pressure or temperature can be accounted for as discussed in greater detail below.

Second, each of the plates 46,48 includes thermal-electric heaters (not shown) that heat the web of skin 52 to a uniform temperature. According to one embodiment of the present invention, the thermal-electric heaters heat the web to about 100° F.±0.1° F. The thermal-electric heaters, which are incorporated into each of the plates, are able to provide very accurate temperature control. Typically, the temperature differential between the surface of skin and the interior ranges between 5-7° F. Heating the skin to a substantially uniform level significantly reduces scattering of the light transmitted through the skin due to temperature gradients resulting in a more consistent analysis. Additionally, heating the skin to about 100° F. expands the capillaries and increases the amount of blood in the capillaries by approximately 300%, thus bringing more glucose into the area of analysis.

As discussed above, the AOTF 16 modulates the beam of light 14, which causes the beam of light transmitted through the skin via the optoid 34 to be modulated. The modulation aids in resolving some of the issues associated with instrument drift that can effect the quality of the spectral information. The modulated, transmitted light is received by the detector 58 and the modulated transmitted light strikes the active material of the detector 58 and is converted by the detector into an electrical current indicative of the light received. According to one embodiment, the electrical signal generated by the detector 58 is amplified by an amplifier (not shown) and sent to a lock-in amplifier 70, which demodulates the signal. A suitable lock-in amplifier 70 is available from Stanford Research Instruments, Model SR 810 DSP, according to one embodiment of the present invention. Alternatively still, the lock-in amplifier is integrated into an integrated circuit board comprising the described electrical hardware of the present invention.

An analog-to-digital converter 72 then digitizes the demodulated signal. According to one embodiment of the present invention, the analog-to-digital converter is a sixteen-bit converter available from National Instruments Corporation of Austin, Tex. Alternatively, digitization is incorporated into an integrated circuit board comprising the described electrical hardware of the present invention. In other alternative embodiments, the digitization is at an 18 bit or higher bit rate.

The spectral data are optionally passed through a high frequency filter 74 to remove high frequency noise and then a low frequency filter 76 to remove slow drifting that occurs due to gradual changes in the patient's skin over the course of the analysis, or drift observed in the instrument or the optical fibers. Filtering the signal in this manner improves the overall signal-to-noise ratio.

The signal is then passed on to a central processing unit ("CPU") 78. The CPU 78 averages the received signal every minute resulting in approximately 500 data sets over an approximately 500 minute test. The data points are then stored in a memory of the CPU 78. The data are saved with a tracking of the wavelength of the light input to the optoid 34 and the corresponding spectral signal produced by the detector 58. The spectral signal is also stored along with the time associated skin temperature, room temperature, pressure applied to the skin during the measurement, and blood pressure measurements. This information is useful in determining whether any irregularities in the spectral signal are the result of changes in these type of factors and not the result of changes in the glucose concentration. The data are then processed to improve the signal-to-noise quality of the data and to remove artifact effects that can corrupt the quality of the spectral data. According to alternative embodiments of the present invention, the processing to improve the signal-to-noise ratio can be accomplished in a variety of manners. For example, in one alternative embodiment, the signal-to-noise quality of the signal is improved by using Wavelet transforms to remove high frequency noise and low frequency baseline drift type of noise (i.e., irrelevant spectral variations that are determined by the information entropy corresponding to glucose levels). According to another alternative embodiment, the signal-to-noise quality is improved using such classical methods such as Savitsky-Golay multipoint smoothing. In other embodiments, first derivative analysis can be used to deal with baseline issues such as baseline drift type of noise.

Additionally, the noise in the signal is improved by removing spectral information that is not related to the relevant glucose information according to alternative embodiments of the present invention. This is accomplished by the application of a Genetic Algorithm for selecting wavelength regions that are the most related to the glucose changes and removing others that are not. This process results in the development of robust calibration algorithms that significantly reduce overfitting issues. In still another alternative embodiments, Orthogonal Signal Correction ("OSC") is employed to aid in the removal of non-glucose spectral information from the signal. This approach has proven beneficial in the removal of temperature and time drift related change imprints on the glucose-related data. Removing the data related to pressure and temperature changes over the course of the analysis results in a better calibration algorithm that results in better glucose predictions based on spectral data. Using a combination of approaches results in a more improved signal than using these different approaches individually. For example, the inventors have found that a combination of Wavelet processing and OSC has produced excellent results. Additionally, the inventors have found that the use of Genetic Algorithms in conjunction with OSC has produced excellent results.

Similarly, the reference detector 14 detects the beam of light 23, which is indicative of the light 14 provided to the optoid, and produces a "reference signal." The reference signal is processed in a manner similar to the signal produced by the detector 58.

Figure 2:
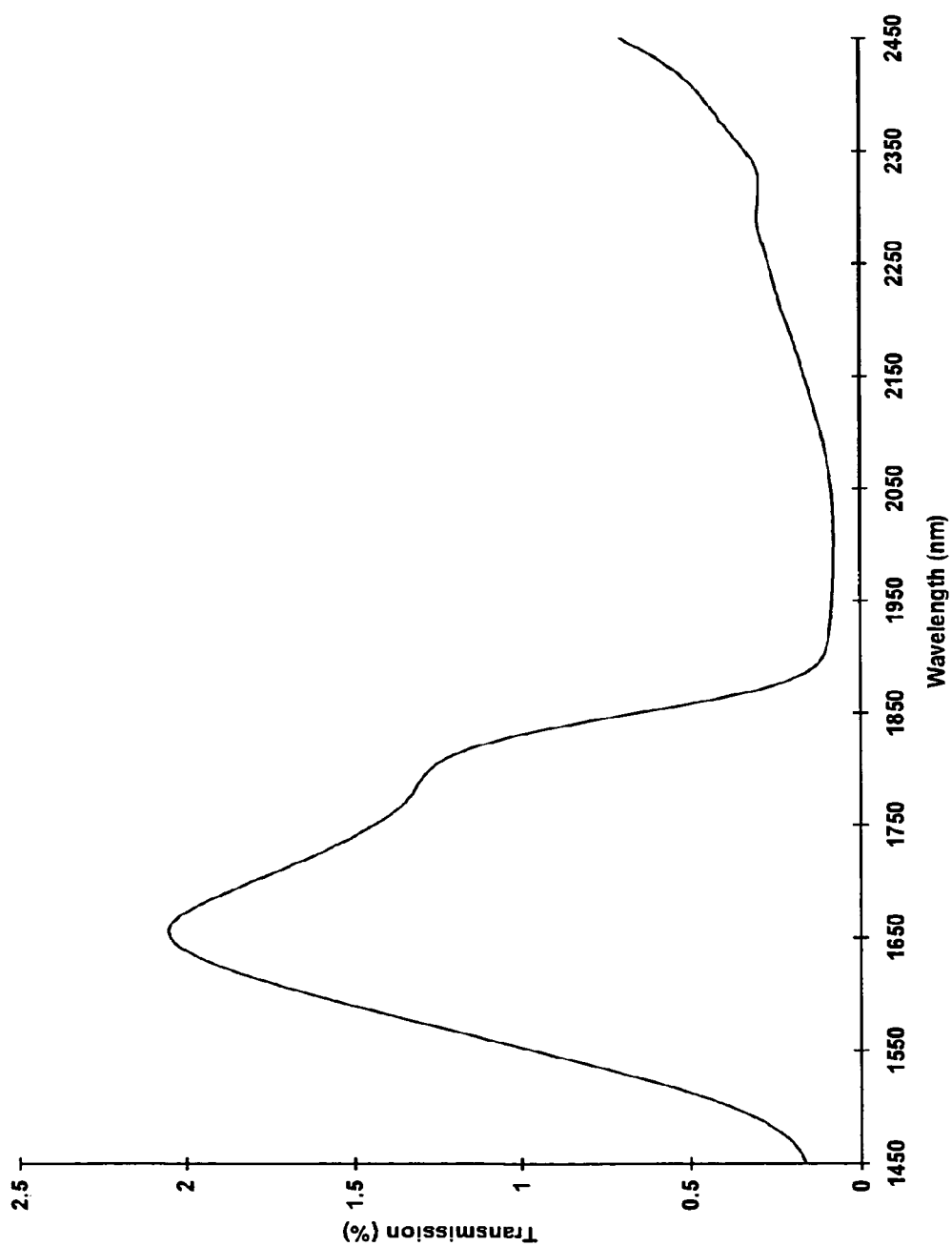
FIG. 2 is a plot of the absorbency of transmitted light versus wavelength of the transmitted light according to one embodiment of the transmission-based system illustrated in FIG. 1.

Referring now to FIG. 2, a plot of the percentage of light transmitted through the web versus wavelength (nm) is shown. The peaks in the plot between from about 1450-1850 nm and about 2200-2500 nm show a high absorbency of light 56 transmitted though the tissue. The high absorbency within these spectral ranges is due, in part, to absorption by the water contained in the skin. The glucose in the skin is present, in large part, where the water in the skin is located. Glucose exhibits unique spectral characteristics within these two wavelength ranges.

As mentioned above, during the glucose clamping test, in addition to the transmitted spectral data, samples of blood and ISF are obtained from the test subject (e.g., the patient subjected to the test) to determine the subject's actual blood glucose level. According to one example of the glucose-clamping test, the test is conducted over an approximately 500 minute duration. The blood and ISF samples are obtained about every 5 minutes, totaling about 100 samples. These values are then interpolated over the 500 minute test duration, resulting in about 500 glucose concentration values.

The digital spectral signal of the transmitted light is averaged every minute and stored resulting in about 500 data sets over the course of the test duration. This data is then analyzed and processed (described in greater detail below) to build a calibration algorithm for predicting the actual glucose concentration level from an examination of the spectral characteristics of the transmitted light.

Figure 3:
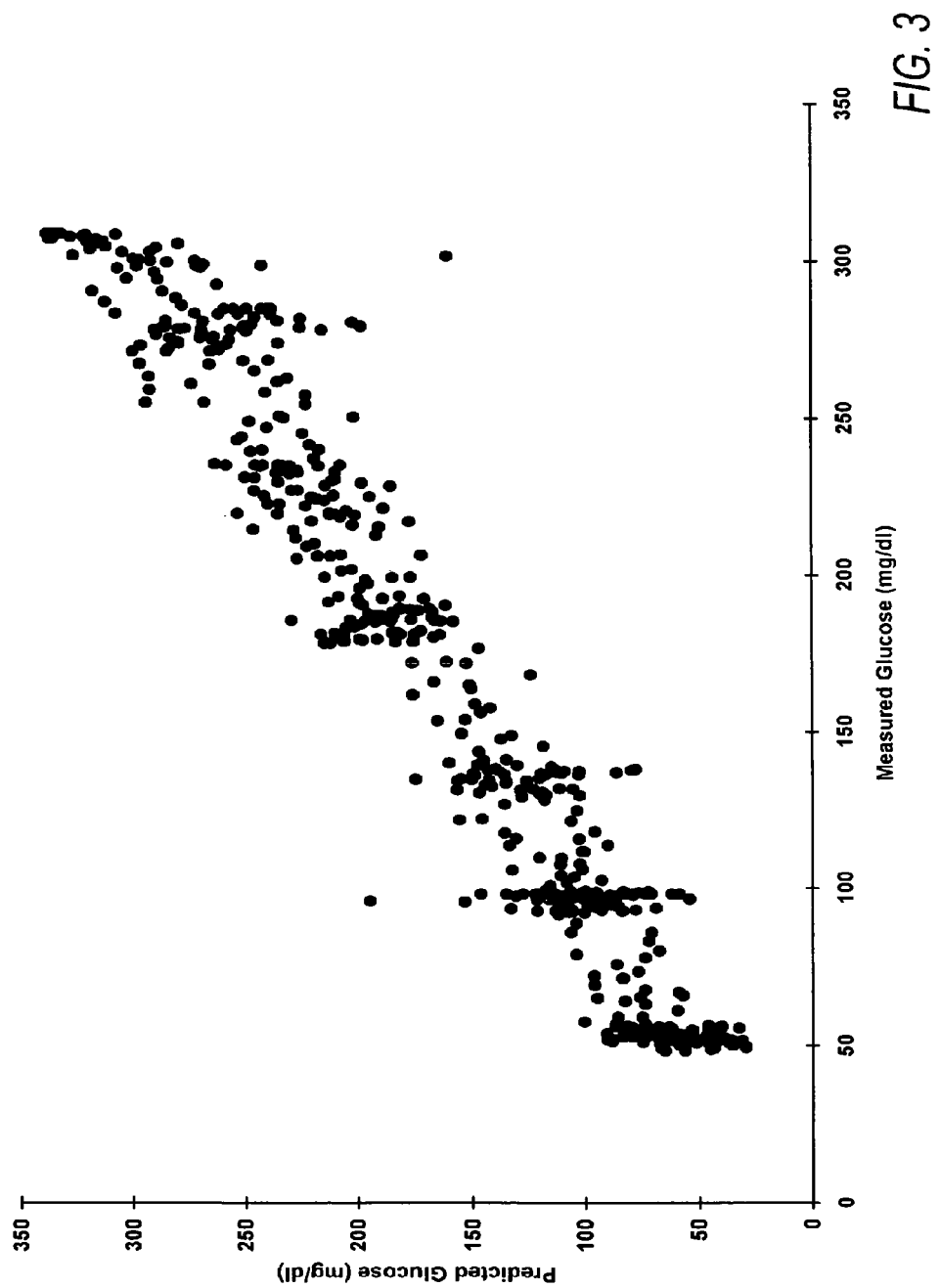
FIG. 3 is a plot of predicted glucose concentration versus the measured glucose concentration according to one embodiment of the transmission-based system illustrated in FIG. 1.

Referring now to FIG. 3, a plot of the predicted glucose value (from spectral characteristics of transmitted light) versus the measured glucose value is shown. As can be seen in the plot of FIG. 3, there is excellent correlation between the predicted glucose concentration and the measured glucose concentration.

In order to obtain the predicted values plotted in FIG. 3, it is necessary to build a calibration algorithm that predicts the glucose concentration from the transmitted spectral signal (i.e., the signal produced by the detector 58). After the spectral signal is filtered by the high and low frequency filters 74,78, the signal is normalized to correct for changes in the spectral signal which are the results of spectral scattering of the light when transmitted through the web 52 and due to the pressure effects of the optoid 34 which is clamped to the web of skin 52. Failure to correct for these changes may obscure the spectral information associated with the glucose. As stated above, less than approximately two percent of the light input to the web of skin 52 is transmitted to the detector 58. Accordingly, it is important to account for these types of changes and irregularities than can lead to errors. The raw signal from the AOTF spectrometer described above is first normalized to constant energy, then mean centered to remove constant areas of the spectrum, creating a normalized, preprocessed series of spectra that are then checked for outliers by standard methods well known in the art. Further preprocessing by OSC reduction and wavelets analysis filtering are done to enhance the glucose signal and to suppress the water and other background signals. The resulting set of spectra is then used to build a calibration model by partial least squares (PLS) regression using Venetian blinds cross-validation on a portion of the data described above or on all of the data. Alternative embodiments to the data preparation described above involve other common methods for reduction or removal of background signal, including, but not limited to, first-derivative smoothing, second-derivative smoothing, wavelength selection by means of genetic algorithms, wavelet processing, and principal components analysis. Alternative embodiments for the generation of calibration models can be realized by many different forms of regression, including principal components regression, ridge regression or ordinary (inverse) least squares regression.

The calibration algorithm to predict the glucose concentration is then built from the normalized signal. An orthogonal signal correction process is combined with the time associated temperature and pressure information to identify the parts of the spectrum that are associated with these factors and not strictly related to the changes in the glucose concentration. This process is used in combination with the correlated data (i.e., the invasively determined glucose concentrations of the plasma and the ISF fluids) to filter out of the spectral data information that is associated with changes in the other measurements and not with changes in the glucose. This results in a calibration algorithm that is much more clearly associated with the changes in the glucose concentration, and less with artifacts that happen to correlate to the glucose concentration. Other data improvement processes include the use of more generic chemometric applications such as Genetic Algorithms and Wavelet analysis to further refine the spectral information to the most efficient information. The Genetic algorithm and Wavelet analysis are able to select wavelengths in the spectrum that are specifically related to glucose and to permit the calibration algorithm to focus on specific changes in the glucose concentration. The selection is based on the area of the spectrum where the strongest glucose related peaks are located, but also the spectral areas related to the changes in the refractive index of the tissue due to changes in the tissue concentration. This wavelength selection process results in retaining the wavelength information that produces the best calibration algorithm.

Figure 4:
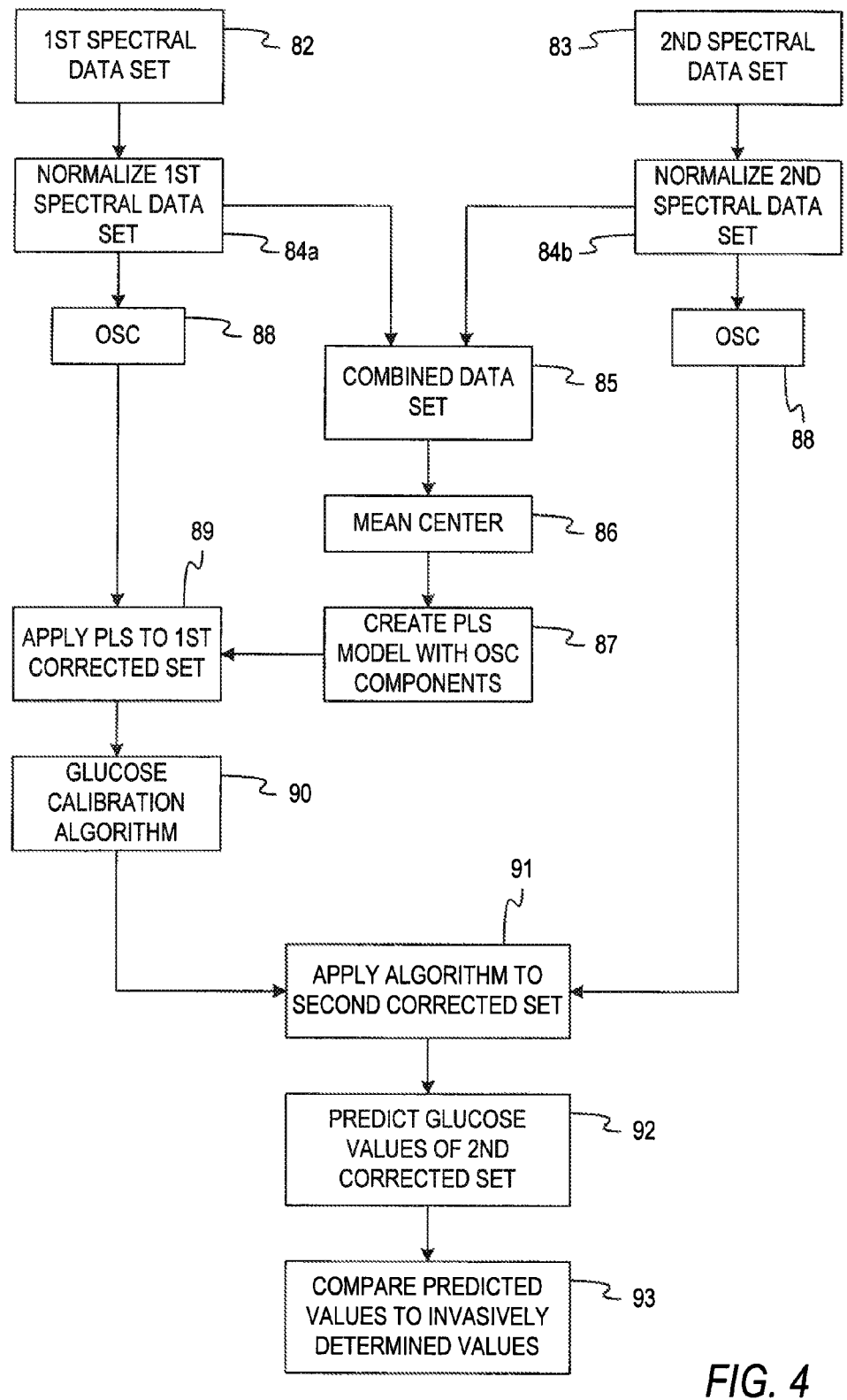
FIG. 4 is a flow chart depicting a method for building a glucose calibration algorithm according to one embodiment of the present invention.

Referring now to FIG. 4, a flow chart depicting a method of building the glucose calibration algorithm will be described according to one embodiment of the present invention. Initially, as described above, a glucose clamping experiment is conducted wherein spectral information is obtained from the body tissue of at least a first and a second test subject. This information is stored in a first data set 82 and a second data set 83. In one embodiment, the first and second data sets 82, 83 each include spectral information obtain from a plurality of test subjects. Other information such as body tissue temperate, pressure applied to the body tissue, and the invasively determined glucose concentration levels are obtained from each of the test subjects at predetermined intervals during the glucose clamping test.

A combined data set, consisting of spectral data from more than one test subjects (e.g., data from the first and second spectral data sets 82, 83), is prepared and used to generate a model useful for prediction of glucose levels for all of the subjects contributing data. The raw signals, stored in the first and second data sets 82, 83, from the AOTF spectrometer described above are first normalized at steps 84a, 84b to constant energy for data from each of the test subjects. Portions of the data for each subject are then combined to form a single, combined spectral set at step 85, which is then mean centered at step 86 to remove constant areas of the spectrum, creating a normalized, preprocessed series of spectra that are then checked for outliers by standard methods known in the art. Further preprocessing by OSC reduction and wavelets analysis filtering are done to enhance the glucose signal and to suppress the water and other background signals. The resulting set of spectra is then used to build a calibration model by partial least squares (PLS) regression as step 87 using Venetian blinds cross-validation on a portion of the data described above or on all of the data. Alternative embodiments to the data preparation described above involve other common methods for reduction or removal of background signal, including, but not limited to, first-derivative smoothing, second-derivative smoothing, wavelength selection by means of genetic algorithms, wavelet processing and principal components analysis. Alternative embodiments for the generation of calibration models can be realized by many different forms of regression, including principal components regression, ridge regression or ordinary (inverse) least squares regression.

The PLS model, which was created at step 87, is applied to the orthogonal signal corrected, normalized first data set at step 89, which results in the glucose calibration algorithm at step 90. The glucose calibration algorithm 90 is used to predict glucose concentration based upon spectral information obtained from a test subject. Put another way, the glucose calibration algorithm is able to determine the glucose concentration of a test subject based upon the spectral information (e.g., transmitted or reflected spectral information) obtained from a test subject. The glucose calibration algorithm 90 is then applied to the orthogonal signal corrected, normalized second data set at step 91 for predicting the glucose contraction values of the test subject(s) of the second spectral data set 83 at step 92. The glucose concentration values predicted at step 92 are then compared to the invasively determined glucose concentration obtained during the glucose clamping test to check the accuracy of the glucose calibration algorithm at step 93.

In an alternative embodiment of the present invention, building the glucose calibration algorithm also includes applying a Wavelets analysis to each of the data sets after OSC step 88, which filters the data. Additionally, in other alternative embodiments of the present invention, the spectral data sets 82, 83 include spectral data modeled for glucose concentration levels which are outside the range of glucose concentration levels achieved during the glucose clamping test. In one embodiment, the AOTF spectrometer 16 can be used to create spectral data outside the ranges achieve during the glucose clamping test.

Figure 5A:
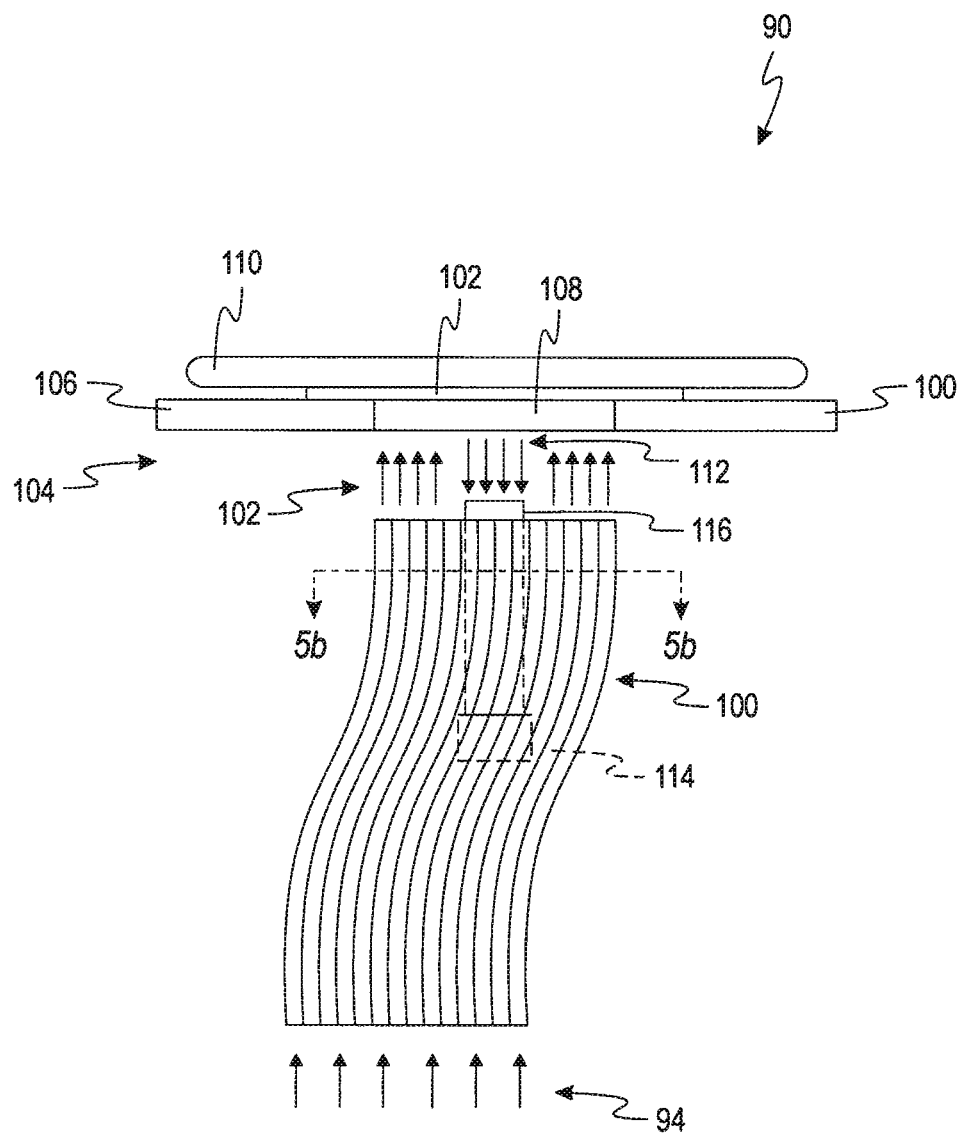
FIG. 5a is a functional block diagram of a reflectance-based system for determining analytes in body fluids according to one embodiment of the present invention.
Figure 5B:
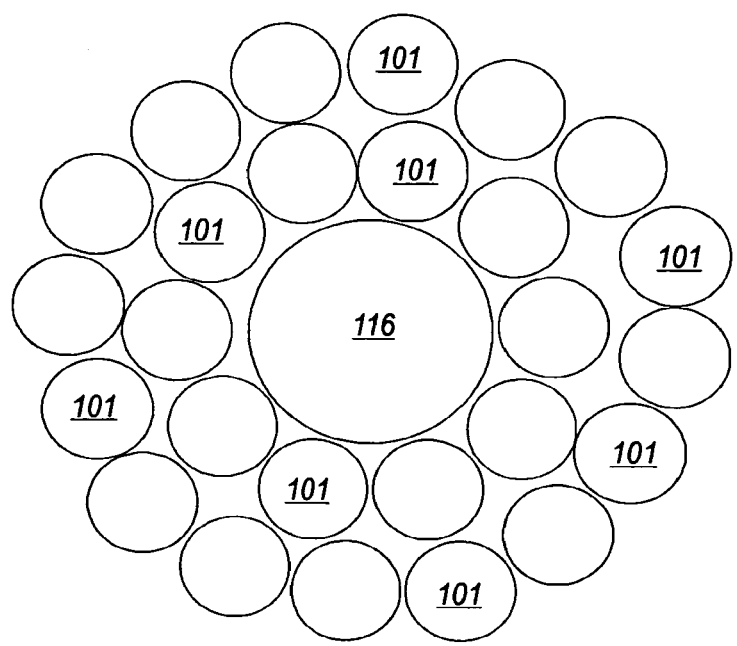

Referring now to FIGS. 5a and 5b, a reflectance-based non-invasive system 90 ("the system 90") for the determination of analytes in body fluids is functionally illustrated. Briefly, the system 90 inputs near infrared light into a portion of a patient's skin, such as a forearm, and records the amount of light reflected from the skin in order to determine the patient's glucose level.

A monochromatic beam of light is input to a bundle 100 of fiber optic cables 101. While the bundle 100 of fiber optic cables depicted in FIG. 5b shows two concentric circles or rows of fiber optic cables 101, any reasonable number of rows of fiber optic cable can be used. The monochromatic beam of light is generated in a manner similar to that described in connection with FIG. 1. An AOTF spectrometer (not shown) outputs a beam of light 94 having a resolution of four to ten nanometers ("nm"), which is swept (back and forth) across a wavelength range of about 2200-4500 nanometers to the fiber optic cable bundle 100. The fiber optic cable bundle 100 delivers light 94 to an optoid 104. The optoid 104 consists of the hardware that interfaces with a patient's skin. The optoid 104 includes a plate 106 having a window 108. Light 102 is directed through the window 108 onto the patient's skin 110. According to one embodiment of the present invention, the window 108 is a sapphire window.

In use, the optoid 104 is brought into contact with a patient's skin 110 such as the patient's forearm, such that skin 110 rests on the plate 106 and window 108. Light 102 is directed through the window 108 into the skin 110. The light penetrates the skin 110 to a depth of about 300 microns and is then reflected from inside the skin 110. The reflected light is represent by arrows 112. The reflected light 112 is directed to a detector 114 via a sapphire rod 116 disposed within the fiber optic bundle 100. The reflected light 112 is detected by the detector 114 in a manner similar to the transmitted light 56 discussed in connection with FIG. 1.

According to an alternative embodiment of the reflectance-based, non-invasive system 90, only a portion of the fiber optic cables 101 are used to deliver light to the optoid 104 which varies the path length of the delivered light. For example, only an inner ring of fiber optic cables 101 be utilized according to one embodiment and only the outer ring of finger optic cables 101 are utilized according to another embodiment. Varying the path length of the delivered allows the sampling of reflected light from different depths in the tissue. According to some embodiments, the various path lengths are used to correct for individual tissue characteristics such as scattering.

The optoid 104 of the reflectance-based non-invasive system 90 provides temperature control to the area of skin from which the reflectance signal is being taken. According to one embodiment of the present invention, the plates 106 of the optoid include thermoelectric heaters for heating the skin to approximately 100°±0.1° F. Again, heating the skin to uniform temperature reduces scattering of light, which is a function of temperature. Additionally, as discussed above, heating the skin causes the capillaries to expand thus increasing the volume of blood in the capillaries approximately three hundred percent.

According to one embodiment of the present invention, an index matching material 112 is disposed between the skin 110 and the sapphire window 108, for maintaining a constant and matched index for the light 102 directed into the skin 110 and the light reflected from the skin 112. The index matching gel reduces large index of refraction changes that would occur normally between skin and a gap of air. These large changes result in Fresnel losses that are especially significant in a reflectance based analysis, which creates significant changes in the spectral signal. According to one embodiment of the present invention, the indexing matching material 112 is a chloro-fluoro-carbon gel. This type of indexing material has several favorable properties. First, the chloro-fluoro-carbon gel minimally impacts the spectral signal directed through the gel. Second, this indexing matching material has a high fluid temperature point so that it remains in a gel-like state during the analysis and under test conditions. Third, this gel exhibits hydrophobic properties so that it seals the sweat glands so that sweat does not fog-up (i.e., form a liquid vapor on) the sapphire window 108. And fourth, this type of index matching material will not be absorbed into the stratum corneum during the analysis.

The output of the detector 114 is filtered and processed in a manner similar to that described in conjunction with the above-described transmission-based system 10.

Figure 6:
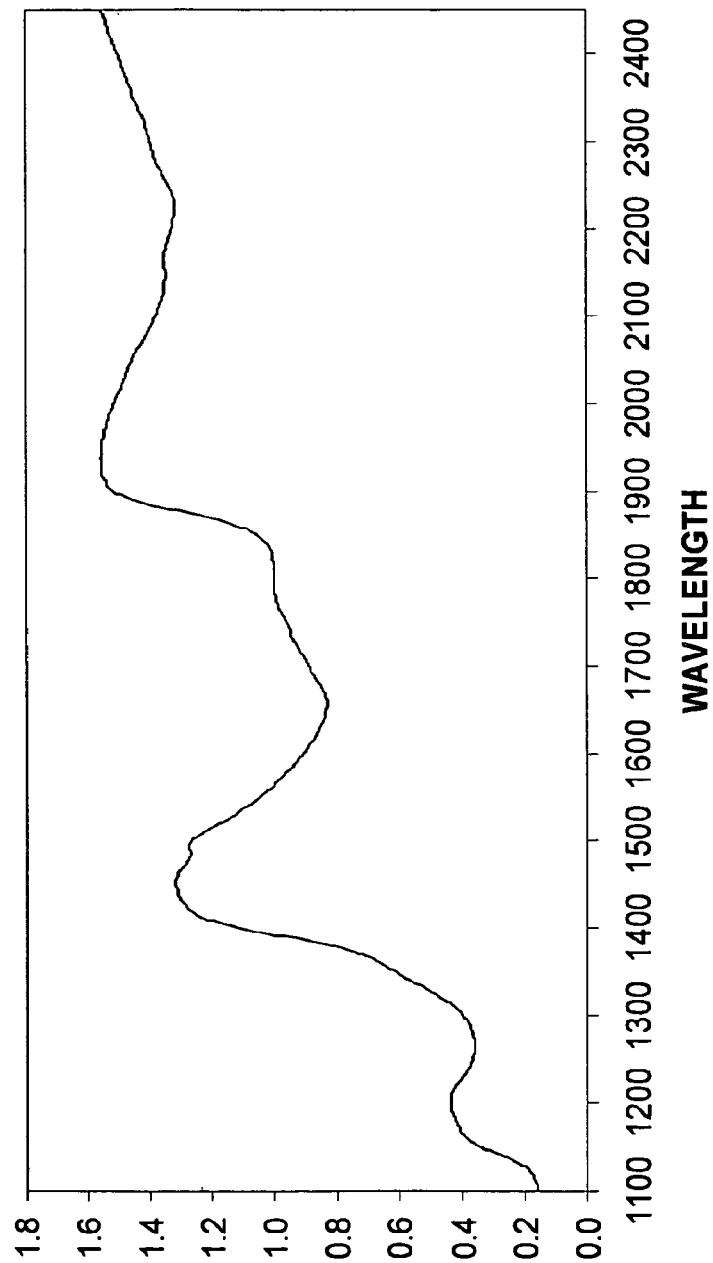

Referring now to FIG. 6, a plot of the absorption of light input to the skin versus wavelength is shown. As can be seen in FIG. 6, high absorption is observed in the 1350-1600 nm and the 1850-2100 spectral range.

Figure 7:
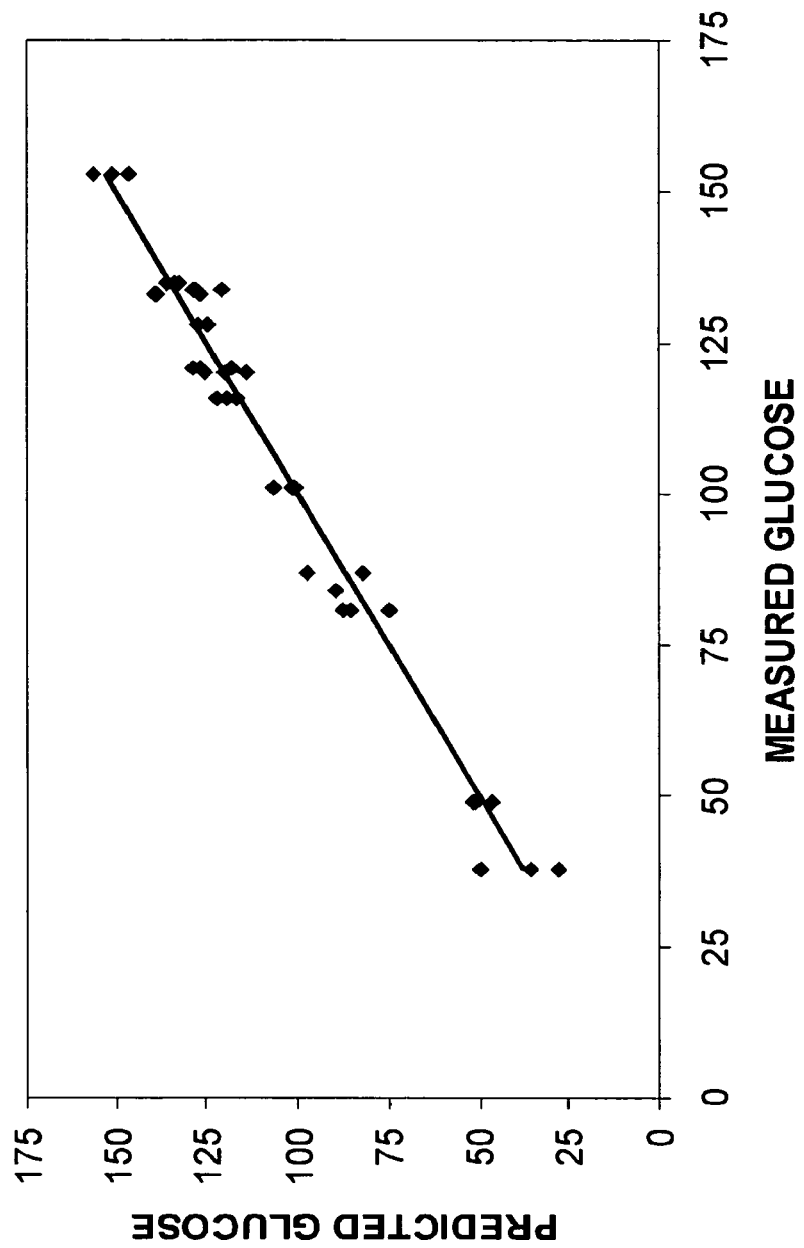

The calibration algorithm for the reflectance-based system is built by applying similar data processing techniques as discussed in connection with the transmission-based system. Referring now to FIG. 7, a plot of the predicted glucose concentration using the calibration algorithm versus the measured glucose concentration (obtained invasively) is shown. As in the case of the transmission-based system 10, the reflectance-based system 90 provides an accurate prediction of the test subject's glucose concentration.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method for converting spectral information obtained from a body tissue into an analyte concentration level in at least one body fluid in the body tissue, wherein the analyte concentration level of the at least one body fluid in body tissue of a plurality of test subjects including a first test subject and a second test subject is modulated to a plurality of predetermined analyte concentration levels within a range of analyte concentration levels, the method comprising the acts of:

invasively determining the analyte concentration levels of the at least one body fluid of each of the test subjects during an analyte clamping test comprising the modulating of analyte concentration levels of the at least one body fluid in body tissue;

directing by an infrared light source infrared light onto the body tissue of the test subjects being analyzed during the analyte clamping test;

collecting spectral information using a detector from the body tissue of the test subjects;

creating, using a spectrometer, modeled spectral information modeled for analyte concentration levels outside the range of analyte concentration levels;

combining the modeled spectral information with the collected spectral information from the body tissue of the test subjects;

normalizing the combined spectral information;

combining by a central processing unit a portion of the normalized spectral information collected from the first test subject with a portion of the normalized spectral information collected from the second test subject to create a combined spectral data set;

the central processing unit mean centering the combined spectral data set;

the central processing unit creating a partial least squares regression model having at least one orthogonal signal correction component from the combined spectral data set, the partial least squares regression model being configured to filter out non-analyte related spectral information from the spectral data set by selecting wavelengths in the spectral data set based on at least changes in a refractive index of body tissue due to changes in tissue concentration;

the central processing unit applying an orthogonal signal correction analysis to the normalized spectral information collected from the first test subject, thereby forming a first corrected data set, and to the normalized spectral information collected from the second test subject, thereby forming a second corrected data set;

the central processing unit applying the partial least squares regression model to the first corrected data set, resulting in a calibration algorithm that is applied to the second corrected data set, and predicting using the calibration algorithm an analyte concentration level in a body fluid in a body tissue of the second test subject based upon the collected spectral information obtained from the body tissue of the second test subject, wherein the analyte is glucose.

2. The method of claim 1, wherein the analyte level concentration in the body fluid in the body tissue of the second test subject is predicted by applying the partial least squares regression model to the second corrected data set.

3. The method of claim 2 further comprising comparing the predicted analyte concentration levels of the at least one body fluid in the body tissue of the second test subject to the invasively determined the analyte concentration levels collected from the second test subject during the test.

4. The method of claim 1 further comprising filtering the first and the second corrected spectral data set by applying a wavelet analysis prior to applying the partial least squares regression model.

5. The method of claim 1 further comprising collecting data other than spectral information during the modulating of analyte concentration levels, the data being selected from the group consisting of a target body fluid analyte concentration for each test subject, temperature of the body tissue for each test subject, pressure applied to the body tissue of each test subject, frequency of the infrared light directed onto the body tissue of each test subject, and time of data collection.

* * * * *